(12) United States Patent
Fries et al.

(10) Patent No.: US 10,252,735 B2
(45) Date of Patent: Apr. 9, 2019

(54) ROUTE MONITORING SYSTEM AND METHOD

(71) Applicant: General Electric Company, Schenectady, NY (US)

(72) Inventors: Jeffrey Michael Fries, Grain Valley, MO (US); Joseph Forrest Noffsinger, Grain Valley, MO (US); Richard Lee Lawson, Melbourne, FL (US); Aric Albert Weingartner, Lee's Summit, MO (US); Curtis Doyle Mechling, Jacksonville, FL (US); Aaron Richard Mitti, Atlanta, GA (US); Martin Paget, Saint Johns, FL (US); William David Shields, Grain Valley, MO (US)

(73) Assignee: GE GLOBAL SOURCING LLC, Norwalk, CT (US)

( * ) Notice: Subject to any disclaimer, the term of this patent is extended or adjusted under 35 U.S.C. 154(b) by 212 days.

(21) Appl. No.: 15/345,158

(22) Filed: Nov. 7, 2016

(65) Prior Publication Data

US 2017/0050653 A1 Feb. 23, 2017

Related U.S. Application Data

(63) Continuation of application No. 14/512,729, filed on Oct. 13, 2014, now abandoned.
(Continued)

(51) Int. Cl.
*B61L 23/00* (2006.01)
*B61L 23/04* (2006.01)
(Continued)

(52) U.S. Cl.
CPC ........... *B61L 23/041* (2013.01); *B61L 1/181* (2013.01); *B61L 1/20* (2013.01); *B61L 15/0036* (2013.01);
(Continued)

(58) Field of Classification Search
CPC ........ B61L 23/044; B61L 1/185; B61L 1/181; B61L 15/0081; B61L 23/04;
(Continued)

(56) References Cited

U.S. PATENT DOCUMENTS 4,117,529 A * 9/1978 Stark ................ B61L 23/044
246/34 R
6,102,340 A * 8/2000 Peek ................. B61L 23/044
246/121
(Continued)

*Primary Examiner* — Jason Holloway
(74) *Attorney, Agent, or Firm* — Christopher R. Carroll; The Small Patent Law Group

(57) ABSTRACT

A monitoring method and system monitor a transmitted current that is injected into conductive components of a route traveled by vehicle systems, monitor a received current that represents a portion of the transmitted current that is conducted through the conductive components of the route, examine changes in the transmitted and/or received current over time to determine when the vehicle systems are on the route between a first location where the transmitted current is injected into the conductive components and a second location where the received current is monitored, and examine the changes in the transmitted and/or received currents. The changes are examined to identify (a) a contaminated portion of a surface on which the route is disposed, (b) a foreign object other than the vehicle systems that is contacting the route, and/or (c) a damaged or broken portion of at least one of the conductive components of the route.

20 Claims, 9 Drawing Sheets

Related U.S. Application Data

(60) Provisional application No. 61/912,069, filed on Dec. 5, 2013.

(51) Int. Cl.
*B61L 1/18* (2006.01)
*B61L 1/20* (2006.01)
*B61L 15/00* (2006.01)
*G01N 27/04* (2006.01)
*G01N 27/20* (2006.01)
*G01V 3/02* (2006.01)
*B61L 3/10* (2006.01)

(52) U.S. Cl.
CPC .......... *B61L 23/044* (2013.01); *G01N 27/041* (2013.01); *G01N 27/20* (2013.01); *G01V 3/02* (2013.01); *B61L 3/10* (2013.01); *B61L 15/0081* (2013.01); *B61L 23/047* (2013.01)

(58) Field of Classification Search
CPC ........ B61L 23/045; B61L 23/047; B61L 3/10; B61L 3/243; B61K 9/10
See application file for complete search history.

(56) References Cited

U.S. PATENT DOCUMENTS

| | | | | |
|---|---|---|---|---|
| 6,262,573 | B1* | 7/2001 | Wojnarowski | B61K 9/10 324/217 |
| 8,914,171 | B2* | 12/2014 | Noffsinger | B61L 23/044 701/19 |
| 2001/0019263 | A1* | 9/2001 | Kwun | G01N 29/11 324/217 |
| 2002/0113170 | A1* | 8/2002 | Grappone | B61L 23/041 246/120 |
| 2007/0132463 | A1* | 6/2007 | Anderson | B61L 1/181 324/713 |
| 2008/0105791 | A1* | 5/2008 | Karg | B61K 9/10 246/120 |
| 2010/0258682 | A1* | 10/2010 | Fries | B61L 3/121 246/1 C |
| 2011/0276285 | A1* | 11/2011 | Alexander | B61L 1/20 702/58 |
| 2013/0284859 | A1* | 10/2013 | Polivka | B61L 27/0055 246/34 R |
| 2016/0009300 | A1* | 1/2016 | Cooper | B61L 3/121 701/20 |

* cited by examiner

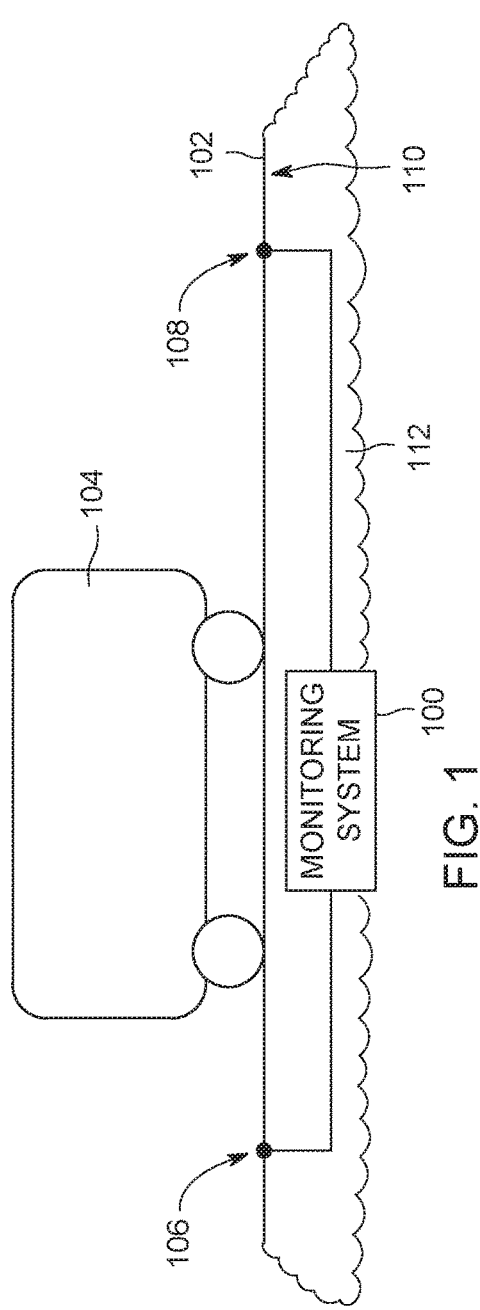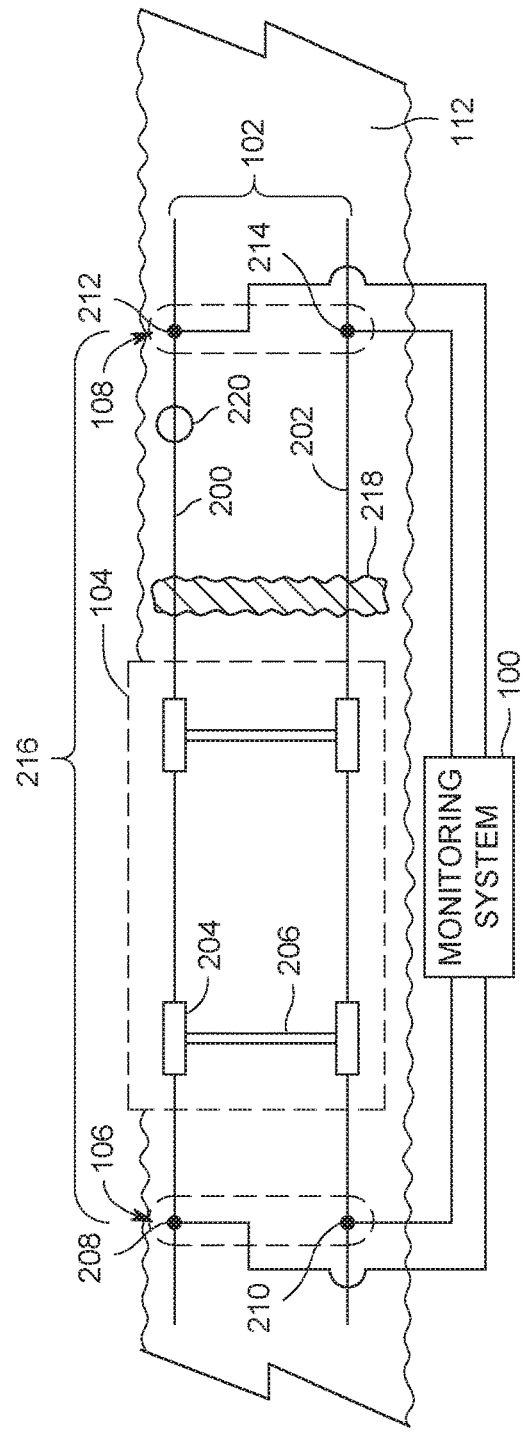

ROUTE MONITORING SYSTEM AND METHOD

CROSS-REFERENCE TO RELATED APPLICATIONS

This application is a continuation of U.S. application Ser. No. 14/512,729, filed 13 Oct. 2014, which claims priority to U.S. Provisional Application No. 61/912,069, which was filed on 5 Dec. 2013, and the entire disclosure of which is incorporated herein by reference.

FIELD

Embodiments of the inventive subject matter described herein relate to electrically monitoring a route traveled by one or more vehicle systems.

BACKGROUND

Some wayside monitoring systems monitor electric current that is conducted in rails of a track to determine when rail vehicles travel on certain segments of the track. When a rail vehicle travels on the segment of the track through which current is being conducted, the rail vehicle can short out a circuit that includes the rails of the track. This shorting of the circuit can be detected so that the presence of the rail vehicle on the track can be automatically detected.

These systems rely on assumptions that no external factors otherwise impact the conduction of current through the rails of the track. For example, if another foreign object or body creates or forms a short or shunt in the circuit that includes the rails of the track, the wayside monitoring system that is monitoring that segment of the track may incorrectly determine that a rail vehicle is on the segment of the track. This incorrect determination can result in disruption of the flow of traffic in a transportation network that includes the track.

For example, after incorrectly identifying a segment of the track as being occupied by a rail vehicle, the wayside monitoring system may automatically change a traffic or warning signal to erroneously indicate to other rail vehicles that the segment of the track is occupied. Additionally or alternatively, the wayside monitoring system may incorrectly notify a dispatch center that the segment of the track is occupied, which can prevent the dispatch center from using that segment of the track to route rail vehicles.

The erroneous identification of a rail vehicle on the segment of track may only be identified by an operator after an extended period of time. Then, one or more persons may be required to travel to the route segment and visually inspect the segment of track to identify the cause of the errors by the wayside monitoring system. The wayside monitoring system may be unable to identify any potential cause for the errors to the persons seeking to repair the problem with the track.

BRIEF DESCRIPTION

In one embodiment, a monitoring method includes monitoring a transmitted current that is injected into conductive components of a route that is traveled by one or more vehicle systems, monitoring a received current that represents at least a portion of the transmitted current that is conducted through the conductive components of the route, examining changes in one or more of the transmitted current or the received current over time to determine when at least one of the vehicle systems is disposed on the route between a first location along the route where the transmitted current is injected into the conductive components and a different, second location along the route where the received current is monitored, and examining the same changes in the one or more of the transmitted current or the received current to identify at least one of a contaminated portion of a surface on which the conductive components of the route are disposed, to identify a foreign object other than the one or more vehicle systems that is contacting the conductive components of the route, or to identify a damaged or broken portion of at least one of the conductive components of the route.

In another embodiment, a monitoring system includes a transmit monitor and a receive monitor. The transmit monitor includes one or more processors configured to measure a transmitted current that is injected into conductive components of a route that is traveled by one or more vehicle systems. The receive monitor includes one or more processors (which may be one or more of the same processors as the transmit monitor or different processors than the transmit monitor) that are configured to measure a received current that represents at least a portion of the transmitted current that is conducted through the conductive components of the route. At least one of the transmit monitor or the receive monitor also is configured to examine changes in one or more of the transmitted current or the received current over time to determine when at least one of the vehicle systems is disposed on the route between a first location along the route where the transmitted current is injected into the conductive components and a different, second location along the route where the received current is monitored. At least one of the transmit monitor or the receive monitor is configured to examine the same changes in the one or more of the transmitted current or the received current to identify at least one of a contaminated portion of a surface on which the conductive components of the route are disposed, to identify a foreign object other than the one or more vehicle systems that is contacting the conductive components of the route, or to identify a damaged or broken portion of at least one of the conductive components of the route.

In another embodiment, a monitoring method includes measuring a transmitted current that is applied at a first location to conductive rails of a track over which one or more rail vehicles travel and measuring a received current at a different, second location to the conductive rails of the track. The received current includes at least a portion of the transmitted current that is conducted through one or more of the conductive rails from the first location to the second location. The method also can include identifying changes in the transmitted current and in the received current over time in order to both identify when the one or more of the rail vehicles travel between the first location and the second location and when at least one of: ballast material disposed between the conductive rails becomes contaminated to at least partially form a short between the conductive rails, a foreign object other than the one or more rail vehicles forms the short between the conductive rails, or one or more of the conductive rails is damaged or broken between the first location and the second location.

BRIEF DESCRIPTION OF THE DRAWINGS

Reference is now made briefly to the accompanying drawings, in which:

FIG. 1 is a schematic diagram of a monitoring system in accordance with one aspect of the inventive subject matter described herein;

FIG. 2 illustrates another schematic diagram of the monitoring system shown in FIG. 1;

DETAILED DESCRIPTION

Figure 3:
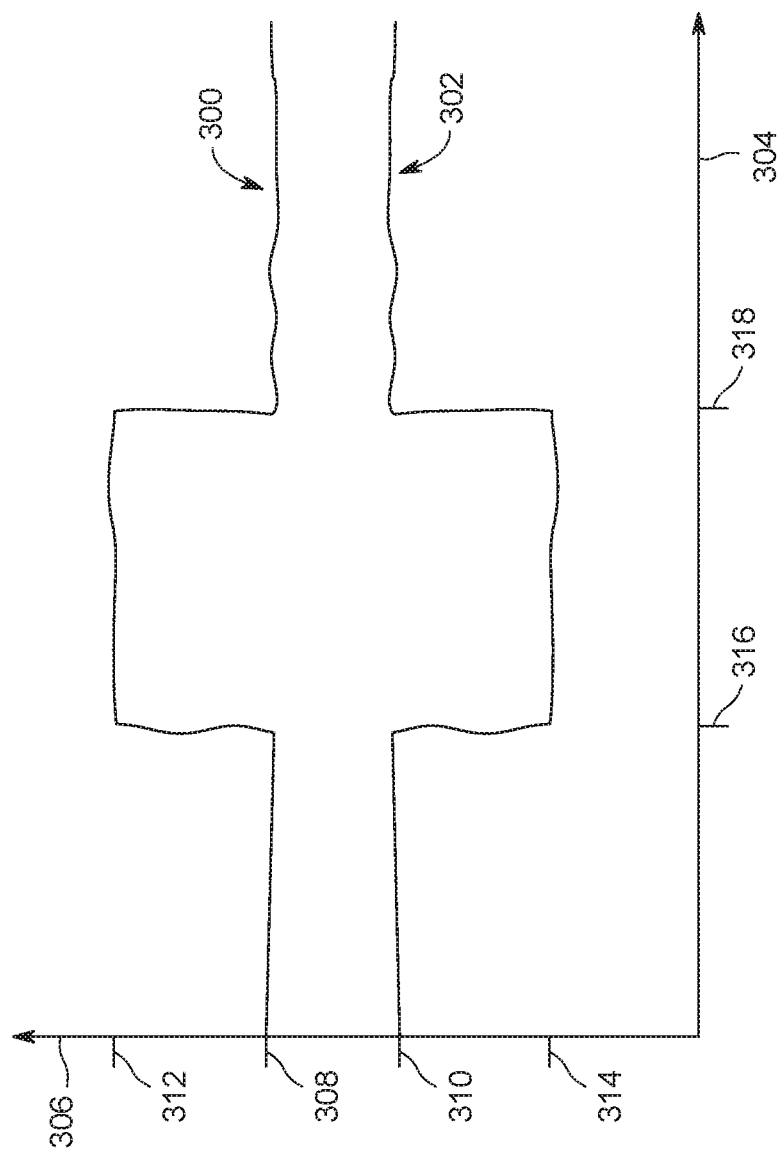
FIG. 3 illustrates changes in a transmitted current that is injected into conductive components of a route shown in FIG. 1 and changes in a received current that is conducted by the conductive components of the route when a vehicle system travels along the route.

One or more embodiments of the inventive subject matter described herein provide monitoring systems and methods that monitor electrical characteristics of a segment of a route on which one or more vehicles may travel. The electrical characteristics are monitored in order to detect the presence of a vehicle system (e.g., a single vehicle, or two or more vehicles mechanically coupled together to travel together along the route, such as in a consist) on the route segment. For example, the route may include plural conductive components (e.g., rails) and the vehicle system may include wheels connected by axles that, when the wheels contact the conductive components of the route, form a conductive pathway or bridge between the conductive components of the route. The systems and methods described herein can monitor changes in electrical characteristics of the conductive components of the route (e.g., changes in an electric current transmitted and received along the conductive components of the route) in order to detect the presence (or absence) of the vehicle system on the route.

Additionally, the systems and methods can examine the electric characteristics over time to identify trends or other changes in the characteristics that may be emblematic of one or more problems with the route. For example, significant increases in an electric current that is injected into the conductive components of the route (which also can be referred to as a transmitted current) and/or significant decreases in an electric current that is received from the conductive components of the route (which also can be referred to as a received current) over an extended period of time can signify that the surface or materials on which the conductive components of the route are positioned (e.g., ballast material) has become contaminated or otherwise damaged (and may need cleaning or replacing). Additionally or alternatively, the systems and methods can determine that the conductive components of the route have been shorted out (e.g., coupled by a conductive pathway other than a vehicle system) based on rapid and significant changes in the transmitted current, the received current, or both the transmitted current and the received current. Optionally, the systems and methods can determine that one or more of the conductive components of the route are damaged (e.g., broken) based on rapid and significant changes in the transmitted current, the received current, or both the transmitted current and the received current.

Once the systems and methods have identified the problems with the surface on which the conductive components of the route are positioned and/or with the conductive components themselves, the systems and methods can take one or more remedial actions. For example, signals can be communicated to one or more locations to request servicing or repair of the surface and/or conductive components of the route, to request modification of an electronic circuit that includes the conductive components of the route, to automatically warn approaching vehicle systems of problems with the surface and/or conductive components of the route, and the like.

One embodiment provides a system and method that measure track circuit parameters at transmit and receive ends of a track circuit that includes conductive rails of a track. The system and method analyze short term and long term trends of the parameters (e.g., current, resistance, voltage, or the like) in order to predict imminent failures of the track circuit so that maintenance is forced or automatically requested to intervene prior to the failure and, when there is a failure, the system and method can identify a type of failure to optimize (e.g., reduce) the cost and timeliness of the response of maintenance to repair the failure.

The system and method can monitor and sample electrical current on the track circuit at each end of the circuit. The sampled values are periodically transmitted to an analysis subsystem (e.g., a transmit monitor, a receive monitor, or both), either wayside on the railway or communicated to a central office. The analysis subsystem identifies trends in the parameters and yields decisions on whether the circuit is performing within bounds or needs maintenance. In an example embodiment, receive current parameters may trend downward during rain, as the track ballast becomes wet and more electrically conductive. Over time, typically in months or years, as ballast stone becomes contaminated with dirt, the dip in receive current when wet becomes more pronounced. When the sampled current meets an alarm threshold (e.g., determined by a learning algorithm or calculated), the risk of a false occupancy of the track circuit increases. The alarm threshold can be set to allow a maintainer to intervene and adjust the circuit before the failure occurs. For example, instead of setting a threshold at a value at which the circuit would incorrectly identify a segment of the track as being occupied, the threshold may be moved downward or upward (as appropriate) so that the contaminated ballast may be identified before the track circuit begins incorrectly determining that the track circuit is occupied by a vehicle system. Over more time, this margin for adjustment will be depleted, and the system or method will determine that the ballast stone needs to be cleaned or refreshed.

In another example, an actual track circuit failure can occur, and the system and method can identify the type of failure, such as a short circuit on the track (e.g., due to scrap metal, failed switch rod insulation, or the like) or a load on the track due to fouled and or wet ballast conditions outside of a current adjustment range (e.g., additional resistive elements cannot be added to the track circuit to reduce the trends in the current, as described below). Depending on the type of failure, the appropriate number of maintainers can be automatically requested or dispatched more efficiently correct the problem.

The erroneous identification of track occupancies can cause railway signals to go red (e.g., stop), which disrupts traffic flow, as well as cause unplanned maintenance expenses. One or more embodiments of the systems and methods described herein predict necessary maintenance for low ballast condition failures, allowing adjustment of the track circuit before failures. If the cause of a failure is determined to be a short circuit, multiple maintainers can be dispatched to walk the track circuit to clear the cause of the failure (e.g., remove scrap metal from a train from the track). If the system or method determines a failure to be due to fouled ballast, only one maintainer may need to be dispatched to make adjustments to the track circuit.

FIG. 1 is a schematic diagram of a wayside monitoring system 100 in accordance with one aspect of the inventive subject matter described herein. The monitoring system includes or represents one or more hardware circuits or circuitry that includes and/or is coupled with one or more processors, controllers, or other electronic logic-based devices that operate to perform various operations described herein. The monitoring system is coupled with a route 102 on which vehicle systems 104 travel along. The route 102 is positioned on a surface 110 formed from one or more materials 112. These materials can be referred to as ballast material, and can include (by way of example only), rock, dirt, or other types of materials. Optionally, the surface and materials may represent another surface that does not include ballast material. Although only a single vehicle system is shown, multiple vehicle systems may concurrently travel along the route. Additionally, the vehicle system 104 is shown as including a single vehicle, but optionally may include multiple vehicles mechanically coupled with each other to travel together along the route, such as in a consist. For example, one or more embodiments of the monitoring system and method described herein may be used in conjunction with a rail vehicle (e.g., rail vehicle consist, train, or the like) that travels along a track (e.g., the route). Optionally, the monitoring system and/or method may be used in conjunction with one or more other types of vehicles and/or routes.

The monitoring system 100 is coupled with the route 102 at two or more spaced apart locations 106, 108. In the illustrated example, one location may be referred to as a transmitting location while the other location may be referred to as a receiving location. The monitoring system may be coupled with the route so that the monitoring system can inject electric signals (e.g., electric currents that are controlled by the monitoring system) into the route at the transmitting location. The monitoring system also may be coupled with the route so that the monitoring system can receive electric signals (e.g., the electric current that is injected into the route at the transmitting location and that is conducted along the route) at the receiving location. For example, the monitoring system may be conductively and/or inductively coupled with the route at the transmitting and receiving locations.

The monitoring system 100 injects the electric signals into the route 102 at the transmitting location 106 or 108 by applying an electric current that is controlled by the monitoring system (e.g., the phase, amplitude, frequency, and the like, is controlled by the monitoring system) to route, such as to the rails of a track. This current can be referred to as a transmitting or transmitted current. The monitoring system can measure the electric current that is conducted along the route at the receiving location 108 or 106. This current can be referred to as a receiving, received, sensed, or measured current. Based on changes in the transmitted current, changes in the received current, and/or differences between the transmitted and received currents, the monitoring system can determine if the vehicle system 104 is traveling along the route between the transmitting and receiving locations along the route. Additionally, the monitoring system can track changes in the transmitted current and/or changes in the received current over time in order to identify and/or predict damage to the route, as described below.

FIG. 2 illustrates another schematic diagram of the wayside monitoring system 100 shown in FIG. 1. In the illustration shown in FIG. 2, the route 102 is shown from a top view so plural conductive components 200, 202 (e.g., rails) of the route 102 are visible. Additionally, the vehicle system 104 is shown in phantom view so that wheels 204 and axles 206 of the vehicle system are visible. The wayside monitoring system can be coupled with the conductive components in the transmitting and receiving locations 106, 108. The wayside monitoring system can be coupled with or include a source of electric energy (e.g., a power source) that applies current to the conductive components at the transmitting location 106. For example, the power source and/or monitoring system can be conductively coupled with the conductive component 200 of the route at a positive terminal 208 and with the conductive component 202 of the route at a negative terminal 210. The transmitted current can be applied to the conductive components across the positive and negative terminal. The monitoring system similarly can be conductively coupled with the conductive components in the receiving location 108 at corresponding first and second terminals 212, 214.

With continued reference to the wayside monitoring system 100 shown in FIGS. 1 and 2, FIG. 3 illustrates changes in a transmitted current 300 that is injected into the conductive components of the route at the transmitting location 106 along the route 102 and changes in a received current 302 that is sensed by the monitoring system at the receiving location 108 along the route when the vehicle system 104 travels across the route. The transmitted and received currents are shown alongside a horizontal axis 304 representative of time (e.g., in terms of minutes or hours) and a vertical axis 306 representative of a magnitude of the transmitted and received currents. For example, the vertical axis can represent different amps of the transmitted and received currents, voltages of the transmitted and received currents (e.g., where the currents are direct currents), or other measurements of the transmitted and received currents.

Prior to entry of the vehicle system 104 onto a segment 216 of the route 102 that is between the transmitting and receiving locations 106, 108 (referred to herein as a route segment under examination or a monitored route segment), the monitoring system 100 may apply the transmitting current 300 to the conductive components 200, 202 of the route in the transmitting location at a first magnitude 308. Due to resistance of the conductive components between the transmitting location and the receiving location, the received current 302 may be sensed by the monitoring location at a smaller, second magnitude 310.

When the vehicle system 104 enters into the examined segment 216 of the route 102 at a time of entry 316, the vehicle system may change one or more of the transmitted and/or received currents 300, 302. For example, the wheels 204 connected to an axle 206 may form a conductive pathway between the conductive components 200, 202 of the route between the transmitting and receiving locations 106, 108. This conductive pathway can form a lower resistance pathway for the transmitted current 300 to travel along in an electronic circuit that includes the conductive components. For example, the wheels and axles can short out the electronic circuit that includes the power source that supplies the transmitted current, the conductive components of the route, and the monitoring system. The short or shunt created by the wheels and axles can result in the transmitted current increasing to a larger, third magnitude 312 due to the decrease in resistance in the circuit caused by the short. For example, the power supply may supply approximately the same voltage (e.g., by direct current or a time-varying voltage that is an alternating current) to the conductive components at the transmitting location, and the lower resistance of the circuit causes the transmitting current to increase while the applied voltage remains the same or substantially the same. The short or shunt created by the wheels and axles can result in the received current 302 decreasing to a smaller, fourth magnitude 314 due to the decrease in transmitted current that is conducted in the circuit to the receiving location. For example, more of the transmitted current may not reach the receiving location due to the short created by the vehicle system.

When the vehicle system 104 exits the examined segment 216 of the route 102 at a time of exit 318, the short created by the vehicle system is no longer present in the circuit that includes the conductive components 200, 202 of the route. As a result, the transmitted current 300 may decrease back to the first magnitude 308 (e.g., due to the increased resistance of the circuit without the short) and the received current 302 may increase back to the second magnitude 310 (e.g., due to more of the transmitted current being conducted to the receiving location 108 when the short is no longer present). The monitoring system 100 can examine the transmitted and/or received currents in order to determine when the examined segment is occupied by the vehicle system.

The time period over which the vehicle system 104 travels over the examined segment 216 of the route 102 (e.g., the time between the time of entry 316 and time of exit 318) can be relatively short, such as on the order of a few minutes or hours. In accordance with one or more aspects of the inventive subject matter described herein, the monitoring system 100 may additionally or alternatively monitor the transmitted and/or received currents 300, 302 over longer periods of time in order to identify and/or predict potential contamination or damage to the route and/or the surface 110 on which the route is positioned. For example, changes in the transmitted and/or received currents over extended periods of time may indicate that the ballast material on which the route is disposed may need to be cleaned and/or replaced, that the route is damaged (e.g., one or more of the conductive components is broken), that a foreign object is on the route, and the like.

As one example, the ballast material 112 on which the conductive components 200, 202 of the route 102 are disposed may become contaminated, such as with materials carried by the vehicle systems that drip or fall onto the ballast material, the ballast material corroding, the ballast material freezing or becoming at least partially submerged in water, or the like. This contamination may cause at least a contaminated portion 218 of the ballast material to increase in conductivity (or otherwise decrease in resistance). For example, the portion of the ballast material that is contaminated may be coupled with the conductive components such that this portion of the ballast material forms a pathway between the conductive components that has a lower resistance that other portions of the ballast material. As a result, at least some of the transmitted current 300 that is injected into the conductive components may be conducted between the conductive components by the contaminated portion of the ballast material and not be sensed as part of the receiving current 302 at the receiving location 108. If enough current is conducted by the contaminated portion of the ballast material, the monitoring system 100 may erroneously determine that a vehicle system is present in the examined segment 216 of the route.

As another example, a portion 220 of one or more of the conductive components 200, 202 of the route 102 may become damaged (e.g., broken through an entire cross-sectional area of the component or through a significant portion of the cross-sectional area). This damage can reduce the amount of transmitted current 300 that is sensed at the receiving location 108 of the route as the receiving current 302. If enough current is unable to be conducted through the damaged portion 220 of the route, then the monitoring system 100 may be unable to determine that a vehicle system 104 is located within the examined section 216 of the route when the vehicle system is present in the examined section of the route.

As another example, a foreign object may be positioned on the route 102 between the conductive components 200, 202 of the route. For example, a chain, bar, pipe, bicycle, or other at least partially conductive object may fall onto the route so that the object engages both of the conductive components of the route within the examined section 216 of the route. The contaminated portion 218 of the ballast material 212 shown in FIG. 2 alternatively may represent such an object. If this object has sufficient conductivity, the object can form a pathway between the conductive components that has a lower resistance than the conductive components between the transmitting and receiving locations 106, 108. As a result, at least some of the transmitted current 300 that is injected into the conductive components may be conducted between the conductive components by the foreign object and not be sensed as part of the receiving current 302 at the receiving location 108. If enough current is conducted by the foreign object, the monitoring system 100 may erroneously determine that a vehicle system is present in the examined segment 216 of the route.

The above are just a few non-limiting examples of external factors (e.g., causes other than the presence of the vehicle system 104 in the examined segment 216 of the route 102) that can change the conductivity of a circuit that includes the conductive components 200, 202 of the route between the transmitting and receiving locations 106, 108. In order to prevent any such change in the conductivity of the circuit from erroneously causing the monitoring system 100 from correctly identifying the presence or absence of the vehicle system in the examined segment of the route, the monitoring system may examine changes in the transmitted and/or received currents 300, 302 over time in order to predict or identify these external factors modifying the transmitted and/or received currents.

Figure 4:
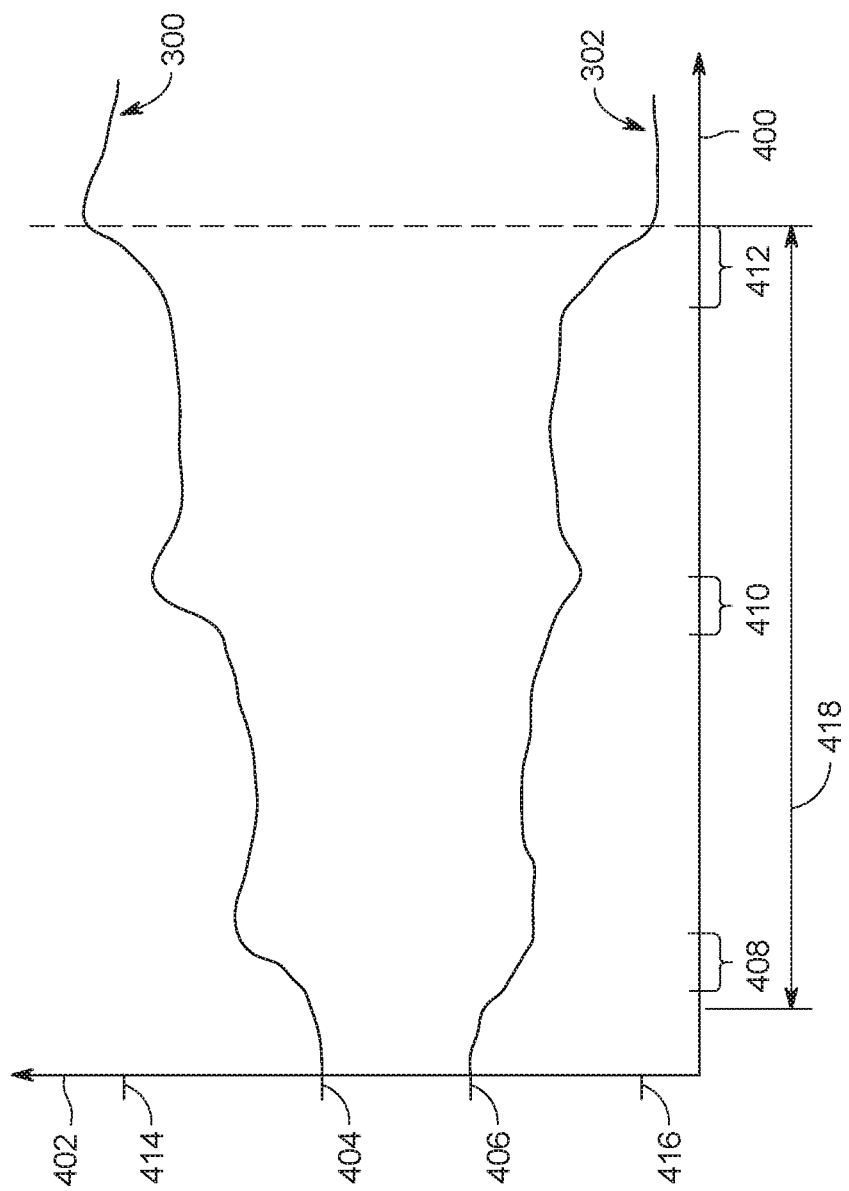
FIG. 4 illustrates examples of changes in the transmitted current and changes in the received current when ballast material on which the route is positioned becomes contaminated.

FIG. 4 illustrates examples of changes in the transmitted current 300 that is injected into the conductive components of the route at the transmitting location 106 along the route 102 and changes in the received current 302 that is sensed by the monitoring system at the receiving location 108 along the route when the ballast material 112 on which the route is positioned becomes contaminated. The transmitted and received currents are shown alongside a horizontal axis 400 representative of time and a vertical axis 402 representative of magnitudes of the transmitted and received currents 302, 304. The horizontal axis shown in FIG. 4 differs from the horizontal axis 304 shown in FIG. 3 in that the horizontal axis of FIG. 4 represents a much longer time period. For example, the horizontal axis in FIG. 3 may represent time periods of several minutes to few hours, while the horizontal axis in FIG. 4 can represent time periods extending over several days, weeks, months, or years. The vertical axis shown in FIG. 4 may be different from the vertical axis 306 shown in FIG. 3 in that the vertical axis of FIG. 4 may encompass much smaller and larger magnitudes of the transmitting and/or receiving currents.

The transmitted and received currents 300, 302 shown in FIG. 4 may be sampled by the monitoring system 100 at various times. For example, instead of continuously measuring the transmitted and received currents, the monitoring system may measure the transmitted and/or received currents periodically (e.g., once every second, every few seconds, every few minutes, every few hours, every few days, or the like) or when directed by an operator or other external event (e.g., a vehicle system leaving the examined segment of the route). Alternatively, the transmitted and/or received currents may be continuously measured by the monitoring system.

As shown in FIG. 4, the transmitted current 300 gradually increases over time from a first magnitude 404 and the received current 302 gradually decreases over time from a second magnitude 406. The first and second magnitudes shown in FIG. 4 may correspond to the corresponding first and second magnitudes 308, 310 shown in FIG. 3. The increases in the transmitted current and/or the decreases in the received current over the extended time period shown in FIG. 4 can be identified by the monitoring system 100 (shown in FIG. 1) as being caused by an external factor other than the presence of a vehicle system 104 (shown in FIG. 1).

The monitoring system 100 can distinguish between relatively rapid rates of change in the transmitting and/or receiving currents 300, 302 and more gradual (e.g., slower) rates of change in the transmitting and/or receiving currents. As shown in FIG. 4, both the transmitting current and the receiving current exhibit faster rates of change (e.g., corresponding increases or decreases) during three corresponding time periods 408, 410, 412, but slower overall rates of change between these time periods. The transmitting current increases from the initial first magnitude 404 to an upper threshold magnitude 414 while the receiving current decreases from the initial second magnitude 406 to a lower threshold magnitude 416.

The monitoring system 100 can ignore the faster rates of change during the time periods 408, 410, 412 but identify the larger changes in the transmitting and receiving currents 300, 302 to the corresponding threshold magnitudes 414, 416 as indicative of the ballast material 112 (shown in FIG. 1) becoming contaminated. For example, if the monitoring system identifies an increase in the transmitting current to the upper threshold magnitude 414 and/or a decrease in the receiving current to the lower threshold magnitude 416, and this increase or decrease occurs over a relatively long threshold time period (e.g., a time period that is longer than the time period of inclement weather, a vehicle system traveling over the examined segment of the route, or the like, such as several days, weeks, or months), then the monitoring system can identify the increase or decrease as being indicative of a contaminated portion 218 of the ballast material, as shown in FIG. 2. The smaller and/or more rapid rates of change in the transmitting and/or receiving currents can be caused by a variety of temporary external factors, such as wet weather conditions (e.g., the ballast material 112 becomes wet or frozen between the conductive components 200, 202 of the route 102). But, because these temporary factors generally do not extend or continue on for the length of time period over which the monitoring system monitors the transmitting and/or receiving currents, the monitoring system can distinguish between temporary changes in the transmitting and/or receiving currents and longer term changes in the transmitting and/or receiving currents.

In one aspect, a temporary change may occur when the transmitting and/or receiving currents vary in value (e.g., magnitude, frequency, or the like) for a time period that is no greater than a designated time period (e.g., one second, five seconds, ten seconds, one minute, five minutes, ten minutes, or another value). Changes in the currents that last at least as long as this designated time period may not be temporary changes in the currents. The length of the designated time period may be adjusted to control the sensitivity of the monitoring system.

The upper and/or lower thresholds may be learned over time. For example, when one examined segment of the route is later identified as having contaminated ballast that is conducting current between the conductive components of the route, the transmitted and/or received currents at which the ballast material is identified as being contaminated may be recorded. This same procedure may be repeated for several segments of one or more routes. The recorded values may be referred to as failure values. An average, median, or other calculation of these values may be used as one or more of the upper and/or lower thresholds. As additional segments have ballast material that becomes contaminated, these thresholds may be updated.

Additionally or alternatively, the weather conditions at or near the monitoring system 100 may be taken into account when examining the transmitted and/or received currents. For example, during wet weather (e.g., rain, snow, sleet, or the like), the resistance of the circuit that includes the conductive components 200, 202 of the route 102 may decrease and/or one or more shorts may form in the ballast material 112 between these conductive components 200, 202 (e.g., by pools of moisture in the ballast material). The system 100 may ignore changes in the transmitted current and/or received current during such weather conditions, as these changes may not be indicative of longer term changes or contamination of the ballast material 112.

The monitoring system 100 can determine that at least a portion of the ballast material 112 that contacts the conductive components 200, 202 of the route 102 is at least partially conducting the transmitted current 300 between the conductive components when the transmitted current increases and/or the received current decreases over a time period that is longer than a time period during which a vehicle system 104 travels or would travel over the route 102 from the transmitting location 106 to the receiving location 108 (or from the receiving location to the transmitting location). The time period during which the vehicle system travels or would travel over this length of the route can be calculated based on the distance between the transmitting and receiving locations and a designated speed of the vehicle system. The designated speed can be a lower speed limit of the route in the examined section 216, such as a minimum speed that the vehicle system is required to travel according to rule, regulation, law, or otherwise.

For example, if the distance between the transmitting location and the receiving location is two miles (e.g., 3.2 kilometers) and the lower speed limit of the route in this segment is twenty miles per hour (e.g., 32 kilometers per hour), then the time period over which a vehicle system should travel over this examined segment or is expected to travel over the examined segment is six minutes. If the monitoring system determines that the transmitted current continues to increase over a longer time period and/or that the received current continues to decrease over a longer time period, then the monitoring system can determine that a portion of the ballast material between the conductive components of the route is at least partially conducting electric current between the conductive components (e.g., is forming a short or a shunt).

The monitoring system can ignore temporary smaller and/or more rapid rates of change in the currents 300, 302, such as the increases or decreases during the time periods 408, 410, 412. These changes can be ignored by the monitoring system because the corresponding increase or decrease in magnitude of the transmitting and/or receiving current is not sufficiently large to exceed the corresponding upper or lower threshold 414, 416, and/or because the rate of change in the currents is faster than a threshold rate of change. For example, even if the transmitting current increases above the upper threshold magnitude and/or the receiving current falls below the lower threshold magnitude, if the increase or decrease in the corresponding current occurs over too short of a time period (e.g., less than a threshold time period), then the monitoring system can disregard the change as being caused by a temporary condition, such as the weather. Increases and/or decreases in the transmitting and/or receiving currents above or below the threshold magnitudes 414, 416 can be identified by the monitoring system as being caused by a contaminated portion 218 (shown in FIG. 2) of the ballast material 112 (also shown in FIG. 2) when the increases and/or decreases occur over a longer period of time, such as a threshold period of time 418. Additionally or alternatively, the weather conditions at the monitoring system 100 can be monitored to determine if the temporary changes in the transmitted and/or received currents are at least partially caused by shorts formed from rain, snow, sleet, or the like, between the conductive components of the route.

Figure 5:
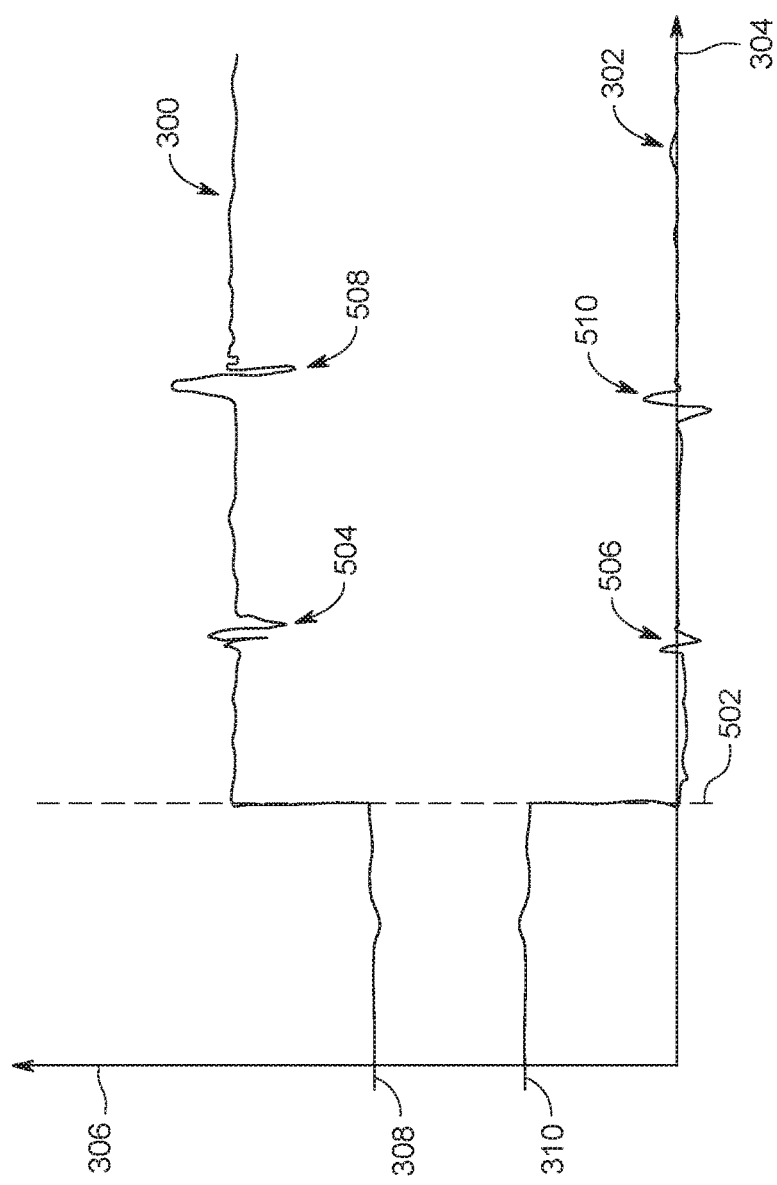
FIG. 5 illustrates examples of changes in the transmitted current and in the received current when a foreign object extends across the conductive components of the route.

FIG. 5 illustrates examples of changes in the transmitted current 300 that is injected into the conductive components of the route at the transmitting location 106 along the route 102 and changes in the received current 302 that is sensed by the monitoring system at the receiving location 108 along the route when a foreign object extends across the conductive components 200, 202 of the route. The transmitted and received currents are shown alongside the horizontal axis 304 and the vertical axis 306 described above. The transmitted and received currents may be sampled by the monitoring system at various times, similar to as described above. Alternatively, the transmitted and/or received currents may be continuously measured by the monitoring system.

As shown in FIG. 5, the transmitted current 300 abruptly increases from the initial first magnitude 308 (e.g., the current applied to the conductive components 200, 202 of the route 102, as described above) to a larger second magnitude 500 at a first time 502 within a relatively short time period, such as within a few seconds or less than one second. The received current 302 similarly decreases from the initial second magnitude 310 (e.g., as described above) to zero current or approximately zero current within the same relatively short time period and/or at the same time 502 that the transmitted current abruptly increases to the second magnitude 500.

Following the abrupt changes in the transmitted and/or received currents 300, 302, the transmitted and received currents remain at or approximately at the same magnitudes for an extended period of time, such as several minutes, hours, or days. This extended period of time can be much longer than the time period over which the transmitted and/or received currents increased to the magnitude 400 or decreased to zero (or approximately zero) current. For example, the transmitted and received currents can maintain constant or approximately constant values for a time period that is several orders of magnitude longer than the time period over which the transmitted and/or received currents abruptly changed. The transmitted and received currents may be "approximately" constant when changes in the currents occur over relatively short time periods and are more indicative of noise in the sampling or measurements of the currents than other causes.

The monitoring system 100 can determine that a foreign object is connecting the conductive components 200, 202 of the route 102 (as described above) responsive to identifying the abrupt increase in the transmitted current 300 and/or the abrupt decrease or elimination of the received current 302. Additionally or alternatively, the monitoring system 100 can determine that the foreign object is connecting the conductive components of the route responsive to (a) identifying the abrupt increase in the transmitted current and/or the abrupt decrease or elimination of the received current, and (b) determining that the transmitted current remains constant or approximately constant for at least a threshold, non-zero period of time following the abrupt increase and/or determining that the received current remains at or approximately at zero current for at least the threshold, non-zero period of time following the abrupt decrease. The monitoring system can determine that the transmitted and/or receive currents remain constant or approximately constant for at least the threshold, non-zero period of time when the changes in the currents last for relatively short periods of time and/or occur at approximately the same or the same time, as is the case for the changes 504, 506 and the changes 508, 510 shown in FIG. 5.

In one aspect, the monitoring system 100 may detect temporary fluctuations or changes 504, 506, 508, 510 in the transmitted and received currents 300, 302 following the abrupt increase and/or decrease in the transmitted and/or received currents. These changes may be larger than noise in the currents that are sensed, and may occur over a relatively smaller period of time. For example, the changes may have magnitudes that are larger than the standard deviation (or another statistical measure or calculation) of the measured current during time periods that follow the abrupt increase or decrease in the current.

The monitoring system can determine whether the temporary changes occur at the same or approximately same time. For example, the monitoring system can determine that the changes 504, 506 in the transmitted and received currents occur at the same or approximately the same time and that the changes 508, 510 in the transmitted and received currents occur at the same or approximately the same time. When the changes 504, 506 and 508, 510 in the transmitted and received currents occur at the same or approximately same time (e.g., the temporary change in the transmitted current occurs during a time period that is the same as or overlaps with a time period during which the temporary change in the received current occurs), the monitoring system may confirm that a foreign object is connecting (e.g., shorting out) the conductive components 200, 202 of the route 102. For example, the temporary changes occurring in the same current may be caused by relatively small movements of the foreign object (e.g., vibration of a conductive body on the tracks due to wind or movement of another nearby vehicle system). Because the same foreign object engages both conductive components to cause the abrupt changes in the transmitted and received currents shown in the example of FIG. 5, temporary movements of the foreign object may be represented by the temporary changes occurring at the same time or approximately the same time in the transmitted and received currents.

Figure 6:
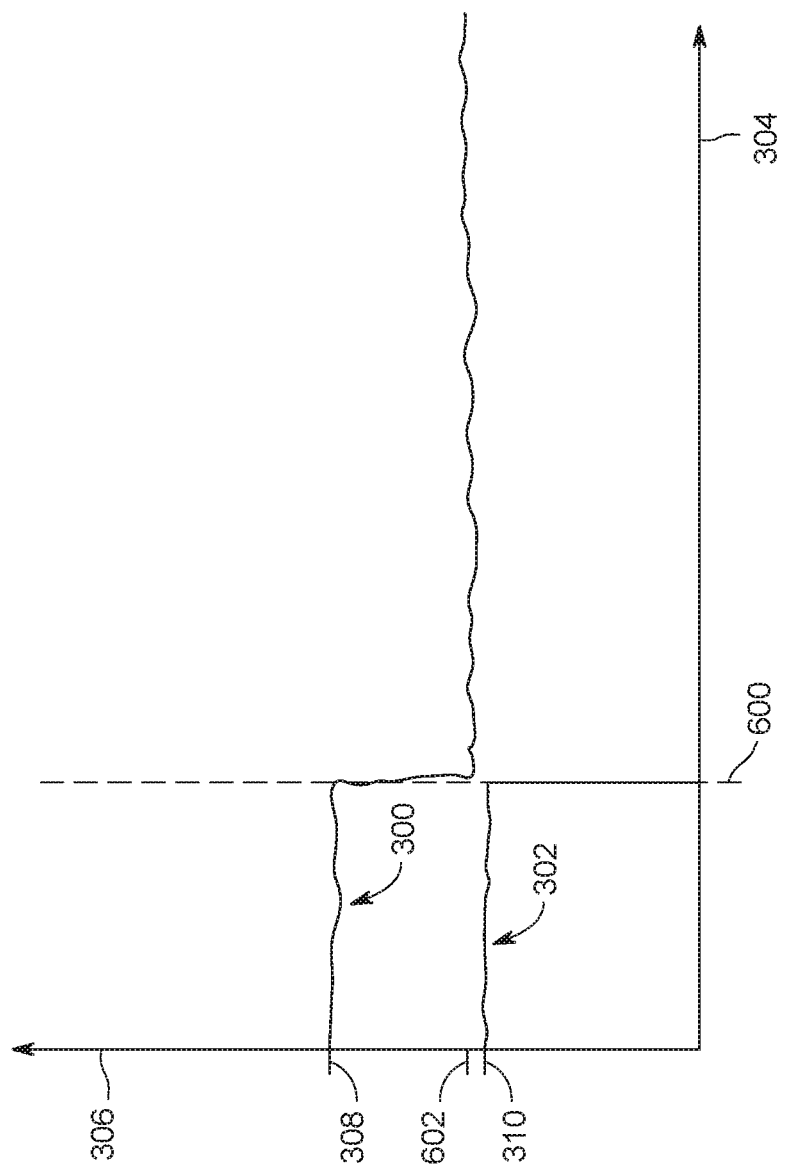
FIG. 6 illustrates examples of changes in the transmitted current and in the received current when one or more of the conductive components of the route are damaged or broken.

FIG. 6 illustrates examples of changes in the transmitted current 300 that is injected into the conductive components of the route at the transmitting location 106 along the route 102 and changes in the received current 302 that is sensed by the monitoring system at the receiving location 108 along the route when one or more of the conductive components 200, 202 of the route are damaged or broken. One or more of these conductive components can be broken when the conductive component is cut or separated through an entire cross-sectional area of the conductive component. For example, a rail of a track is completely broken when a segment of the rail that previously was a continuous or contiguous section of the rail is separated into two separate sections spaced apart by a gap. A conductive component of the route can be damaged when the conductive component is cut or separated through part, but less than all, of the entire cross-sectional area of the conductive component. For example, a rail of a track is damaged but not broken when a segment of the rail is partially separated into two separate sections, but is still at least partially connected.

The transmitted and received currents 300, 302 are shown in FIG. 6 alongside the horizontal axis 304 and the vertical axis 306 described above. The transmitted and received currents may be sampled by the monitoring system at various times, similar to as described above. Alternatively, the transmitted and/or received currents may be continuously measured by the monitoring system.

As shown in FIG. 6, both of the transmitted and received currents 300, 302 abruptly decrease at a time 600. The transmitted current may decrease from the initial first magnitude 308 (e.g., the current applied to the conductive components 200, 202 of the route 102, as described above) to a smaller second magnitude 602 within a relatively short time period, such as within a few seconds or less than one second. The received current 302 also abruptly decreases from the initial second magnitude 310 (e.g., as described above) to zero current or approximately zero current within the same relatively short time period and/or at the same time 600. In the illustrated example, the transmitted current decreases to the second magnitude 602 which is larger than the initial magnitude 310 of the received current, but alternatively may decrease to a second magnitude that is smaller than the initial magnitude of the received current. The time 600 may indicate when one or more of the conductive components were damaged or broken.

Following the abrupt changes in the transmitted and/or received currents 300, 302, the transmitted and received currents remain at or approximately at the same magnitudes for an extended period of time, such as several minutes, hours, or days. This extended period of time can be much longer than the time period over which the transmitted and/or received currents decreased at the time 600. For example, the transmitted and received currents can maintain constant or approximately constant values for a time period that is several orders of magnitude longer than the time period over which the transmitted and/or received currents abruptly decreased. The transmitted and received currents may be "approximately" constant when changes in the currents occur over relatively short time periods and are more indicative of noise in the sampling or measurements of the currents than other causes.

In the illustrated example, the received current 302 is eliminated or substantially eliminated at the time 600. For example, following the time 600, the monitoring system 100 may no longer detect or sense any received current at the receiving location 108 along the route 102 (as shown in FIG. 1). While the monitoring system may detect or sense some current at the receiving location due to noise or hysteresis, the monitoring system may not detect or sense a measurable received current. This lack of detection of the received current following the time 600 can indicate that one or more of the conductive components 200, 202 in the route was damaged or broken at the time 600. For example, the monitoring system may no longer be able to detect the received current because a break in a rail or significant damage to the rail may prevent the received current from being detected in the receiving location 108 of the route. Although the monitoring system may be monitoring the route at plural terminals 212, 214 (shown in FIG. 2), the received current that is measured may be a difference between the currents sensed at these terminals 212, 214 or otherwise indicative of the electric energy sensed at these terminals 212, 214 such that the break or damage in one of the conductive components 200 or 202 causes the received current to be eliminated, as shown in FIG. 6.

The monitoring system 100 can determine that one or more of the conductive components 200, 202 is broken or damaged responsive to identifying the abrupt decrease in the transmitted current 300 and/or the abrupt decrease or elimination in the received current 302 at the same time 600 or at approximately the same time. Additionally or alternatively, the monitoring system can determine that one or more of the conductive components 200, 202 is broken or damaged responsive to identifying the elimination in the received current 302, regardless of changes in the transmitted current 300.

In one aspect, the monitoring system 100 may distinguish between a foreign object being on the route 102 (e.g., described above in connection with the example shown in FIG. 5) from a break or damage to the conductive component 200 and/or 202 in the route based on the presence or absence in the intermittent temporary changes 504, 506, 508, 510 in the transmitted and/or received currents 300, 302. For example, if no intermittent and temporary changes are sensed in the transmitted and/or received currents 300, 302, then the monitoring system can determine that the route has been broken or damaged. If intermittent and temporary changes occurring at the same or approximately same time in the transmitted and received currents are sensed, then the monitoring system may determine that there is a foreign object on the route. Additionally or alternatively, the monitoring system may distinguish between a foreign object on the route and damage or a break in the route based on whether the transmitted current increases or decreases when the received current decreases. If both the transmitted and received currents decrease at the same time or approximately the same time, then the monitoring system may determine that the route is broken or damaged. If the transmitted current increases while the received current decreases, the monitoring system may determine that a foreign object is on the route.

The monitoring system 100 may distinguish between (a) contamination of the ballast material 112 (shown in FIG. 1 and described above in connection with the example shown in FIG. 4) and (b) a foreign object on the route 102 (e.g., described above in connection with the example of FIG. 5) or damage or a break in the route (e.g., described above in connection with FIG. 6) based on the trends in the transmitted and/or received currents 300, 302. For example, the increases in the transmitted current and/or the decreases in the received current that can occur when the ballast material is contaminated may occur over much longer time periods (e.g., days, weeks, months, or years) than the increases or decreases in the transmitted and/or received currents when a foreign object is on the route and/or the route is broken or damaged.

The monitoring system 100 can distinguish between the presence of the vehicle system 104 (shown in FIG. 1) on the route 102 (described above in connection with FIG. 3) and contamination of the ballast material 112 (described above in connection with FIG. 4) based on the trends in the transmitted and/or received currents 300, 302. For example, the increases in the transmitted current and/or the decreases in the received current that can occur when the ballast material is contaminated may occur over much longer time periods (e.g., days, weeks, months, or years) than the increases or decreases in the transmitted and/or received currents when the vehicle system is in the examined segment of the route.

The monitoring system 100 can distinguish between the presence of the vehicle system 104 (shown in FIG. 1) on the route 102 (described above in connection with FIG. 3) and a foreign object being on the route 102 (described above in connection with FIG. 5) based on the change in the received current 302, the duration of the changes in the transmitted and/or received currents 300, 302, and/or the temporal correlation between the temporary changes 504, 506 and 508, 510 (shown in FIG. 5). For example, the received current may not decrease to zero current or approximately zero current when the vehicle system is detected on the route, but may decrease to zero current or approximately zero current when the foreign object is on the route. The transmitted and/or received currents may respectively increase and decrease for a shorter period of time when the vehicle system is detected on the route than when the foreign object is on the route. For example, the transmitted current may increase and the received current may decrease and remain increased or decreased until the foreign object is removed. The temporary changes in the transmitted and received currents may not occur at the same or approximately same times (e.g., which indicates temporal correlation between the temporary changes) when the vehicle system is detected on the route, but may occur when a foreign object is on the route.

The problems or faults that may be identified or predicted by the monitoring system 100 are not limited to those problems or faults described herein. For example, changes in the transmitted current and/or received current may be associated with other faults. Over time, historical changes in the transmitted current and/or received current can be associated with various problems or faults with examined segment 216 of the route 102. These historical changes can be compared with newly obtained transmitted currents and/or received currents in order to determine if the changes in the newly obtained transmitted currents and/or received currents more closely match one or more of the historical changes. If so, then the problems or faults associated with the historical changes that match the newly obtained currents may be identified as a problem or fault. For example, additional failures such as foreign currents interfering with a circuit that includes the conductive components of the route (e.g., currents coming from faults on an adjacent electrified segment of the route, a defective cathodic protection system on a buried pipeline, or the like), defective insulated joints of the route, or other problems may be identified by comparing the transmitted currents and/or received currents with historical data.

Figure 7:
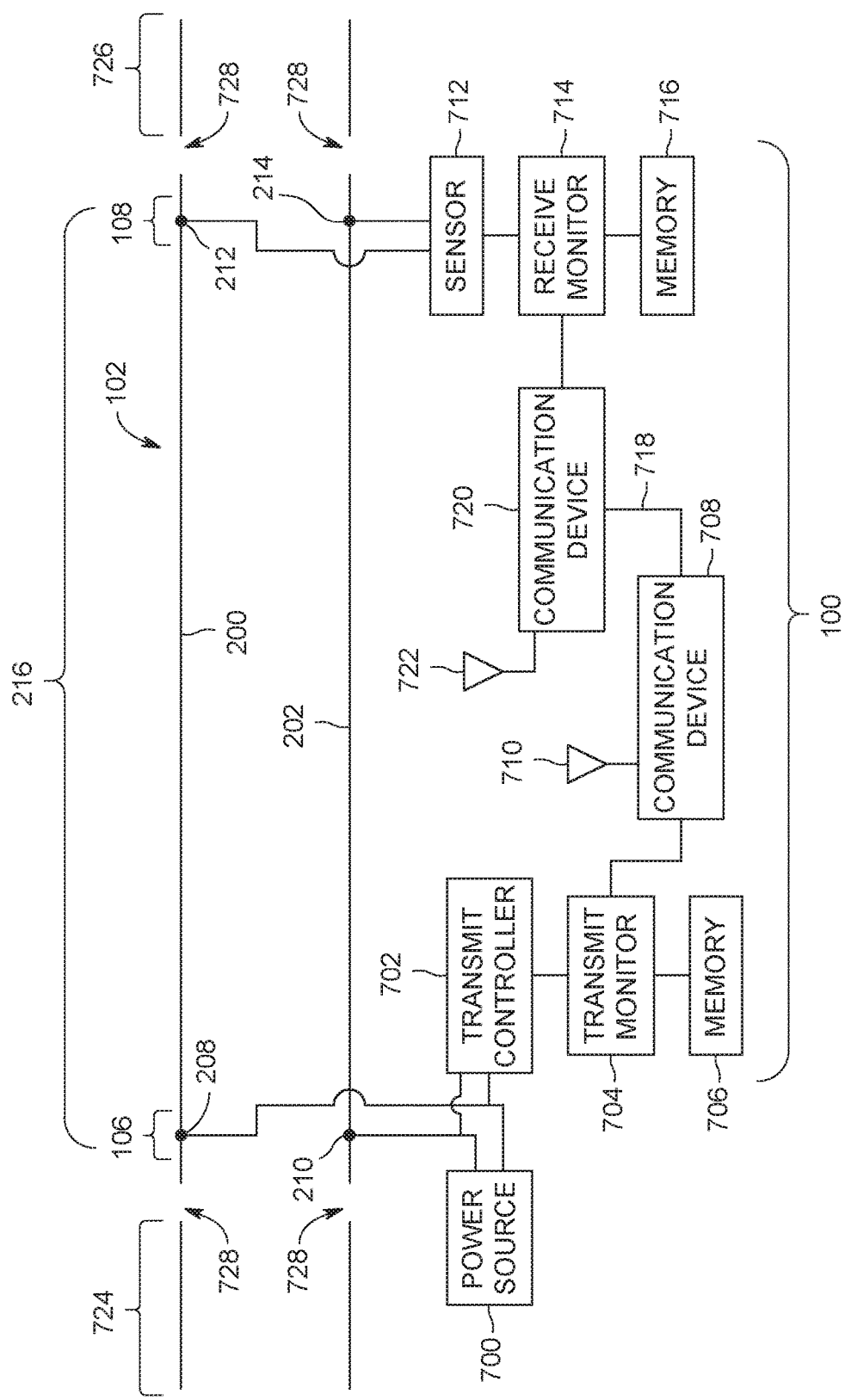
FIG. 7 is another schematic illustration of the monitoring system shown in FIG. 1.

FIG. 7 is another schematic illustration of the monitoring system 100 shown in FIG. 1. The example of the monitoring system in FIG. 7 provides additional details about components that may be included in the monitoring system in one embodiment. The monitoring system includes or is connected with a power source 700, such as one or more utility power grids, batteries, fuel cells, capacitors, flywheels, generators, alternators, or other sources of electric current. The power source provides electric current that is applied to the conductive components 200, 202 of the route 102 in the transmitting location 106 by the monitoring system.

A transmit controller 702 of the monitoring system controls the electric current that is applied to the route by the power source. The transmit controller includes or represents hardware circuits or circuitry that includes or is connected with one or more processors or other electronic logic-based devices that operate to perform the functions of the transmit controller. The transmit controller can control the magnitude (e.g., volts, amps, power, or the like), waveform, frequency, or the like, of the transmit current supplied from the power source, such as by operating one or more switches or other devices that are included in or coupled with the transmit controller.

A transmit monitor 704 of the monitoring system measures the transmitted current that is applied to the route by the power source. The transmit monitor includes or represents hardware circuits or circuitry that includes or is connected with one or more processors or other electronic logic-based devices that operate to perform the functions of the transmit monitor. The transmit monitor can be coupled with the route at the same terminals 208, 210 where the transmit current is applied to the route, and/or can be coupled with the route in another location in order to measure the transmit current. In one aspect, the transmit monitor can include a voltmeter, amp meter, or combination thereof, that measures the transmit current.

A memory 706 of the monitoring system includes one or more devices that can store the transmit currents measured by the transmit monitor. For example, the memory can include one or more computer hard drives, flash drives, magnetic tapes, optical discs, or the like. The memory can store the measured transmit currents over time for analysis or examination.

A communication device 708 of the monitoring system includes transceiver hardware and/or circuitry that includes or is connected with one or more transceiver devices 710 (e.g., an antenna, modem, or the like) that communicate signals with one or more other communication devices. In the illustrated example, the transceiver device is an antenna that wirelessly communicates (e.g., transmits, broadcasts, and/or receives) signals. Optionally, the transceiver device may be coupled with one or more conductive pathways 718 (e.g., cables, catenaries, rails, or the like) to communicate signals through the conductive pathways.

A sensor 712 of the monitoring system is coupled with the route in the receiving location 108 to measure the received currents conducted through the conductive components of the route. The sensor may include or represent a voltmeter, amp meter, or combination thereof, that measures the receive current. The sensor can be connected with the route by the terminals 212, 214.

A receive monitor 714 of the monitoring system measures the received current that is conducted through the conductive components of the route. The receive monitor is connected with the sensor to monitor the received current. The receive monitor can include or represent hardware circuits or circuitry that includes or is connected with one or more processors or other electronic logic-based devices that operate to perform the functions of the receive monitor.

Another memory 716 of the monitoring system includes one or more devices that can store the received currents measured by the receive monitor. For example, the memory can include one or more computer hard drives, flash drives, magnetic tapes, optical discs, or the like. The memory can store the measured received currents over time for analysis or examination. In one embodiment, the memories 706, 716 can be combined into a single memory.

Another communication device 720 of the monitoring system includes transceiver hardware and/or circuitry that includes or is connected with one or more transceiver devices 722 (e.g., an antenna, modem, or the like) that communicate signals with one or more other communication devices. In the illustrated example, the transceiver device is an antenna that wirelessly communicates (e.g., transmits, broadcasts, and/or receives) signals. Optionally, the transceiver device may be coupled with the one or more conductive pathways 718 (e.g., cables, catenaries, rails, or the like) to communicate signals through the conductive pathways. The communication devices 708, 720 can communicate with each other so that the transmitted and/or received currents can be stored in one or more of the memories 706, 716, and/or for the transmit monitor and/or receive monitor to track changes in the transmitted and/or received currents.

The transmit monitor and/or receive monitor can monitor the transmitted and/or received currents as described above in order to determine when a vehicle system 104 (shown in FIG. 1) enters into the examined segment 216 of the route, when the ballast material 112 (shown in FIG. 1) needs to be cleaned or replaced, when a foreign object is on the route, when the route is broken or damaged, and the like. The communication devices can be used so that the transmit monitor is aware of the received currents and/or the receive monitor is aware of the transmitted currents. Optionally, only one of the transmit monitor or the receive monitor examines the transmitted and received currents to determine when a vehicle system enters into the examined segment of the route, when the ballast material needs to be cleaned or replaced, when a foreign object is on the route, when the route is broken or damaged, and the like. Additionally or alternatively, one or more of the transmit monitor or the receive monitor may be disposed at a remote location for remotely examining the transmitted and/or received currents as described above in order to determine when a vehicle system enters into the examined segment of the route, when the ballast material needs to be cleaned or replaced, when a foreign object is on the route, when the route is broken or damaged, and the like.

In the illustrated example, the examined segment 216 of the route 102 is between additional segments 724, 726 of the route. The segments 216, 724, 726 are spaced apart from each other by electrically insulative gaps 728. The insulative gaps prevent the conductive components in the neighboring segments of the route from being conductively coupled with each other. The neighboring segments 724, 726 also may be connected with separate monitoring systems that are similar to the monitoring system 100 described herein. Each of these monitoring systems can examine the transmitted and/or received currents in order to determine when a vehicle system enters into the corresponding segment of the route, when the ballast material beneath the corresponding segment of the route needs to be cleaned or replaced, when a foreign object is on the route in the corresponding segment, when the corresponding segment of the route is broken or damaged, and the like, as described above.

In one embodiment, two or more of the monitoring systems that monitor different segments of the route can communicate with each other in order to identify causes of changes in the transmitted and/or received currents. For example, a first monitoring system that is located upstream of a second monitoring system along the route can communicate with the second monitoring system in order to determine if changes in transmitted and received currents represent the movement of a vehicle system along route, a foreign object on the route, damage or a break in the route, or the like. The monitoring systems can communicate the transmitted and received currents with each other. If the transmitted and received currents measured by the monitoring systems change in a serial or sequential manner, then the changes in the transmitted and received currents may indicate movement of a vehicle system instead of another cause.

Figure 8:
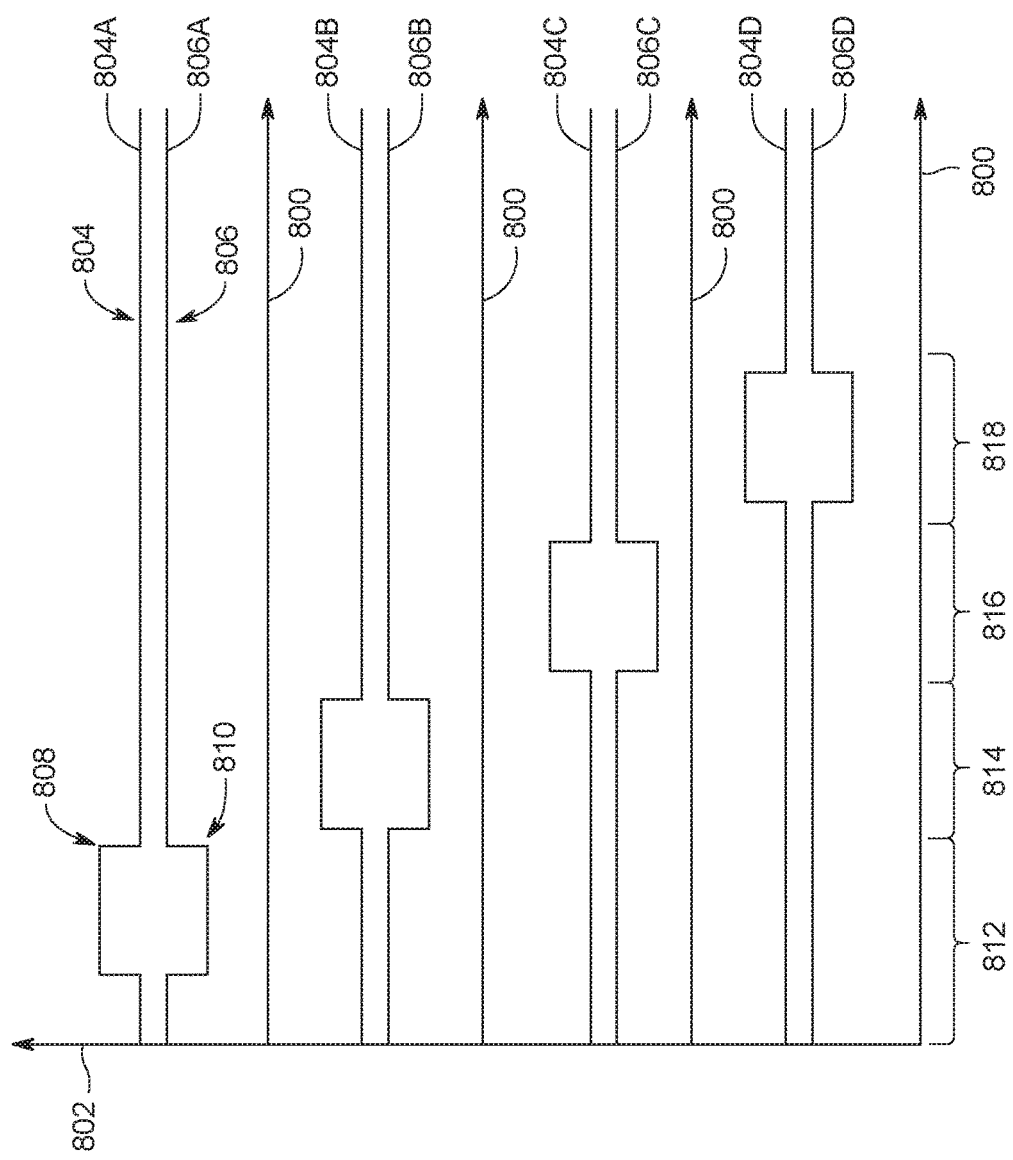
FIG. 8 illustrates transmitted and received currents that are measured by several monitoring systems connected with different segments of the same route in accordance with one embodiment.

FIG. 8 illustrates transmitted and received currents 804, 806 that are measured by several monitoring systems 100 connected with different segments of the same route in accordance with one embodiment. The currents 804, 806 are shown alongside a horizontal axis 800 representative of time and vertical axes 802 representative of magnitudes of the transmitted and received currents.

The transmitted and received currents 804A, 806A are measured by a first monitoring system 100 that is coupled with a first segment of the route 102, the transmitted and received currents 804B, 806B are measured by a second monitoring system 100 that is coupled with a second segment of the route 102 located downstream from the first segment along a direction of travel of a vehicle system, the transmitted and received currents 804C, 806C are measured by a third monitoring system 100 that is coupled with a third segment of the route 102 located downstream from the second segment along a direction of travel of a vehicle system, and the transmitted and received currents 804D, 806D are measured by a fourth monitoring system 100 that is coupled with a fourth segment of the route 102 located downstream from the third segment along a direction of travel of a vehicle system. Additional or fewer monitoring systems and segments may be used.

As a vehicle system 104 travels along the route 102, the monitoring systems detect changes 808, 810 in the transmitted and received currents 804, 806, as described above in connection with FIG. 3. As shown in FIG. 8, these changes 808, 810 occur sequentially among the different segments and monitoring systems. These sequentially spaced changes 808, 810 can indicate that the vehicle system is moving along the route, with the vehicle system traveling over the first segment during a first time period 812, over the second segment during a second time period 814, over the third segment during a third time period 816, and over the fourth segment during a fourth time period 818.

The monitoring systems can communicate the transmitted and received currents 804, 806 with each other (and/or another signal that indicates the presence of the vehicle system in the segments of the route being monitored by the monitoring systems) so that the monitoring systems can distinguish between changes in the transmitted and received currents that represent the presence of the vehicle system versus other causes in the changes. For example, changes in the transmitted and received currents caused by contaminated ballast material 112 may not sequentially occur among the different segments of the route, changes in the transmitted and received currents caused by a foreign object on the route may not sequentially occur among the different segments of the route, and changes in the transmitted and received currents caused by damage or a break in the route may not sequentially occur among the different segments of the route. The monitoring systems can communicate with each other to avoid incorrectly identifying movement of a vehicle system with contaminated ballast material, a foreign object on the route, damage to the route, a break in the route, or the like.

Figure 9A:
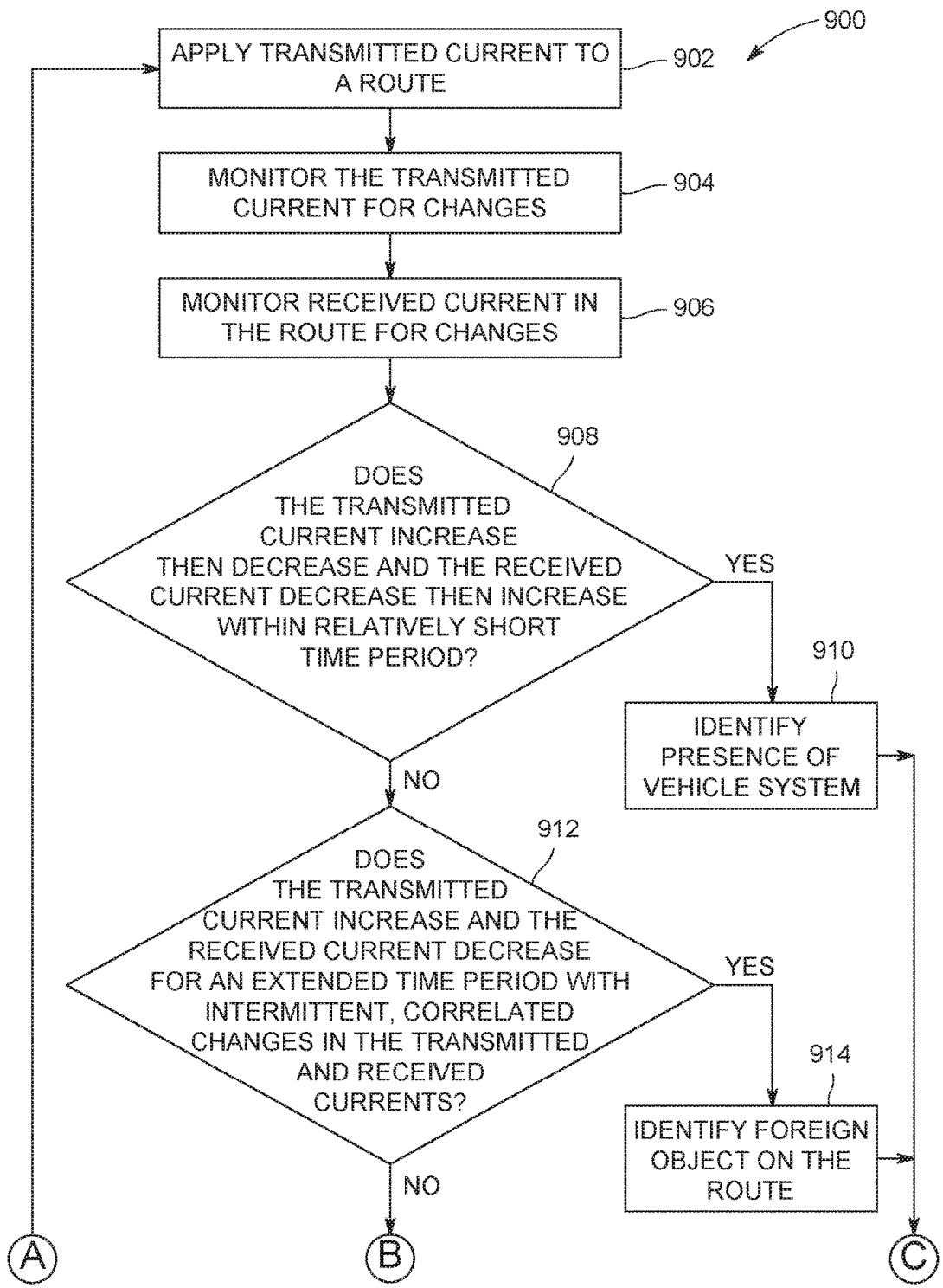
FIGS. 9A and 9B illustrate a flowchart of a method for monitoring a segment of a route in accordance with one embodiment of the inventive subject matter.
Figure 9B:
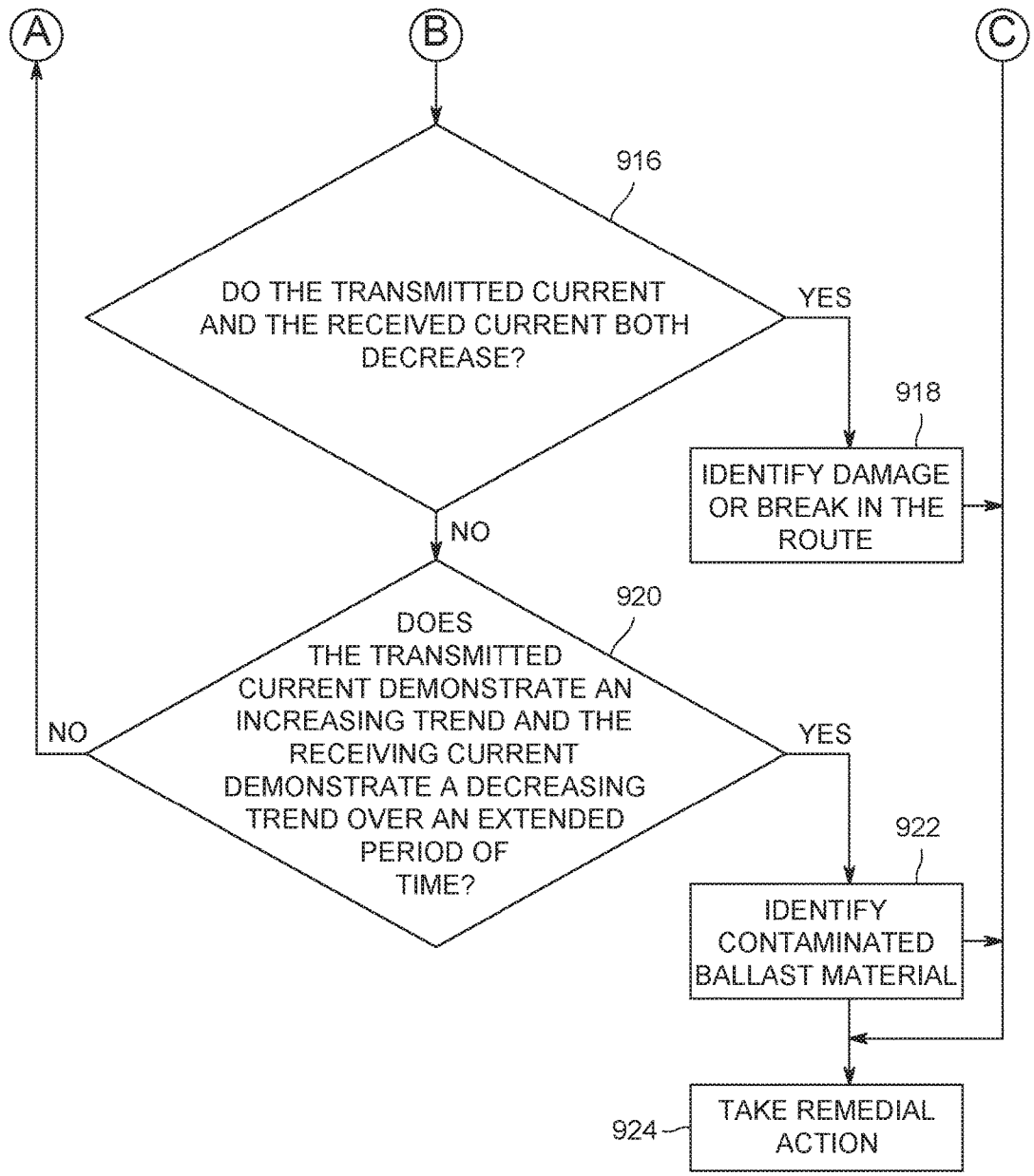

FIGS. 9A and 9B illustrate a flowchart of a method 900 for monitoring a segment of a route in accordance with one embodiment of the inventive subject matter. The method may be used by the monitoring system 100 (shown in FIG. 1) to monitor the examined segment 216 (shown in FIG. 2) of the route 102 (shown in FIG. 1). Although several different monitoring methodologies are described and shown herein, the monitoring system and method may use several or all of these methodologies at the same time.

At 902, electric current is applied to conductive components of a route as a transmitted current. This current can be an alternating current, a direct current, or another type of current. At 904, the transmitted current is monitored. For example, the amps, voltage, frequency, or other characteristic of the transmitted current may be measured or otherwise tracked over time in order to identify changes in the transmitted current.

At 906, current that is conducted along the conductive components of the route to a receiving location is monitored as a received current. For example, the amps, voltage, frequency, or other characteristic of the transmitted current may be measured or otherwise tracked over time in order to identify changes in the received current.

At 908, a determination is made as to whether the transmitted current increased and then decreased and/or the received current decreased and then increased within a relatively short time period. For example, as shown above in the example of FIG. 3, the travel of a vehicle system along the examined segment of the route can cause the transmitted current to increase at the same time or approximately the same time that the received current decreases, followed by the transmitted current decreasing at the same or approximately the same time that the received current increases, within a relatively short period of time. In the event of these changes to the transmitted and received currents, the monitoring system may determine that a vehicle system is located in or has traveled over the examined segment of the route. As a result, flow of the method 900 continues to 910. On the other hand, if the transmitted current and/or received current does not change in this way, then the monitoring system may determine that the changes in the transmitted current and/or received current do not indicate the presence of a vehicle system in the examined section of the route. As a result, flow of the method 900 proceeds to 912.

At 910, the presence of the vehicle system in the examined segment of the route is identified by the monitoring system. The monitoring system can report this presence of the vehicle system to one or more other locations, such as another monitoring system (as described above), to a signal to warn other vehicle systems of the presence of the vehicle system on the examined segment of the route, or the like. At 924, the monitoring system can take one or more remedial or responsive actions, such as reporting the presence of the vehicle system to another location.

At 912, a determination is made as to whether the transmitted current increases and the received current decreases for an extended period of time, and/or if intermittent temporary changes in the transmitted current are temporally correlated with similar changes in the received current. For example, as described above in connection with the example of FIG. 5, the monitoring system may determine if the transmitted current increases and the received current decreases (or is substantially eliminated) at the same time or approximately the same time. The monitoring system also may determine if temporary changes 504, 506, 508, 510 in the transmitted and received currents occur at the same time or approximately the same time. If the monitoring system identifies such changes in the transmitted and received currents, the changes may indicate a foreign object is connected to the conductive components of the route and may be shorting out the circuit that includes the conductive components. As a result, flow of the method 900 may proceed to 914. Otherwise, the changes in the currents may not indicate the presence of a foreign object, and flow of the method 900 can proceed to 916.

At 914, a foreign object is identified as connecting the conductive components of the route by the monitoring system. At 924, the monitoring system can take one or more remedial or responsive actions, such as reporting the presence of the foreign object to another location to schedule or request that an operator or maintainer travel to the location of the examined segment of the route to remove the foreign object. Optionally, the monitoring system can communicate a signal to other vehicle systems or signals to warn the vehicle systems or change the status of the signal to prevent travel of the vehicle systems onto the examined segment of the route.

At 916, a determination is made as to whether the transmitted current and the received current decrease. For example, the monitoring system may determine whether the transmitted current decreases and the received current decreases (or is eliminated) at the same time or approximately the same time. These changes in the transmitted current and received current may indicate that the route is damaged or broken within the examined segment, as described above in connection with FIG. 6. In one aspect, the monitoring system may determine if the transmitted current decreases and the received current reduces to zero (or approximately zero) current for an extended period of time, such as several minutes or hours. If the monitoring system identifies these changes in the transmitted and/or received currents, the monitoring system can determine that the route has been damaged or broken. As a result, flow of the method 900 may proceed to 918. On the other hand, if these changes are not identified, then the transmitted currents and received currents may not indicate that the route is damaged or broken. As a result, flow of the method 900 can proceed to 920.

At 918, the examined segment of the route is identified as being broken or damaged, as described above, by the monitoring system. At 924, the monitoring system can take one or more remedial or responsive actions, such as reporting the damage or break in the route to another location to schedule or request that an operator or maintainer travel to the location of the examined segment of the route to repair or examine the route. Optionally, the monitoring system can communicate a signal to other vehicle systems or signals to warn the vehicle systems or change the status of the signal to prevent travel of the vehicle systems onto the examined segment of the route.

At 920, a determination is made as to whether the transmitted current demonstrates an increasing trend and/or the received current demonstrates a decreasing trend over an extended period of time. For example, the monitoring system can examine the transmitted current and/or the received current over one or more hours, days, weeks, months, or years in order to determine if the transmitted current is gradually increasing while the received current also is gradually decreasing. If the transmitted current is exhibiting such an increasing trend and/or the receiving current is exhibiting such a decreasing trend over an extended time period, then these trends in the transmitted and received currents may indicate that the ballast material beneath the conductive components of the route is forming a short or shunt that is at least partially conducting current between the conductive components. As a result, flow of the method 900 can proceed to 922. On the other hand, if the transmitted current is not exhibiting such an increasing trend and/or the received current is not exhibiting such a decreasing trend, then the transmitted and received currents may not indicate that the ballast material is forming a short or shunt. As a result, flow of the method 900 can return to 902.

At 922, the monitoring system can identify the ballast material as being contaminated in that the ballast material is at least partially conducting current between the conductive components of the route. At 924, the monitoring system can take one or more remedial or responsive actions, such as reporting the contaminated portion of the ballast material to another location to schedule or request that an operator or maintainer travel to the location of the examined segment of the route to replace, clean, or otherwise repair the ballast material. Optionally, the monitoring system can communicate a signal to other vehicle systems or signals to warn the vehicle systems or change the status of the signal to prevent travel of the vehicle systems onto the examined segment of the route. In one aspect, the monitoring system can communicate a request to an off-board location that the examined segment of the route be repaired, such as by adding a resistive element (e.g., one or more resistors), in order to change the electric characteristics of the circuit that includes the conductive components of the route in the examined segment of the route. Adding such a resistive element can reduce or eliminate the increasing trend in the transmitted current and/or the decreasing trend in the received current.

In one embodiment, a wayside monitoring method includes monitoring a transmitted current that is injected into conductive components of a route that is traveled by one or more vehicle systems, monitoring a received current that represents at least a portion of the transmitted current that is conducted through the conductive components of the route, examining changes in one or more of the transmitted current or the received current over time to determine when at least one of the vehicle systems is disposed on the route between a first location along the route where the transmitted current is injected into the conductive components and a different, second location along the route where the received current is monitored, and examining the same changes in the one or more of the transmitted current or the received current to identify at least one of a contaminated portion of a surface on which the conductive components of the route are disposed, to identify a foreign object other than the one or more vehicle systems that is contacting the conductive components of the route, or to identify a damaged or broken portion of at least one of the conductive components of the route.

In one aspect, the changes that are examined to both determine when at least one of the vehicles is disposed on the route and to identify the at least one of the contaminated portion, the foreign object, or the damaged or broken portion of the at least one of the conductive components of the route include increases or decreases in the transmitted current and the received current and time periods over which the increases or decreases in the transmitted current and the received current occur.

In one aspect, the contaminated portion of the surface includes a portion of ballast material disposed beneath the conductive components of the route that at least partially conducts the transmitted current between the conductive components of the route through the contaminated portion of the surface.

In one aspect, the foreign object that is identified is one or more conductive bodies forming a short between the conductive components of the route.

In one aspect, the damaged or broken portion of the at least one of the conductive components of the route includes a portion of the at least one of the conductive components that is separated through an entire cross-sectional area of the at least one of the conductive components.

In one aspect, the contaminated portion of the surface on which the conductive components of the route are disposed is identified when the changes in the transmitted current and in the received current include an increasing trend in the transmitted current over an extended period of time that concurrently occurs with a decreasing trend in the received current over the extended period of time.

In one aspect, the foreign object is identified when the changes in the received current include a decrease in the received current to zero current or approximately zero current and temporary changes in the received current that are temporally correlated with temporary changes in the transmitted current.

In one aspect, the damaged or broken portion of the at least one of the conductive components of the route is identified when the changes in the transmitted current and in the received current include a decrease in the transmitted current that occurs concurrently with an elimination of the received current.

In one aspect, the route includes a track over which rail vehicles travel and the conductive components include rails of the track.

In another embodiment, a wayside monitoring system includes a transmit monitor and a receive monitor. The transmit monitor includes one or more processors configured to measure a transmitted current that is injected into conductive components of a route that is traveled by one or more vehicle systems. The receive monitor includes one or more processors (which may be one or more of the same processors as the transmit monitor or different processors than the transmit monitor) that are configured to measure a received current that represents at least a portion of the transmitted current that is conducted through the conductive components of the route. At least one of the transmit monitor or the receive monitor also is configured to examine changes in one or more of the transmitted current or the received current over time to determine when at least one of the vehicle systems is disposed on the route between a first location along the route where the transmitted current is injected into the conductive components and a different, second location along the route where the received current is monitored. At least one of the transmit monitor or the receive monitor is configured to examine the same changes in the one or more of the transmitted current or the received current to identify at least one of a contaminated portion of a surface on which the conductive components of the route are disposed, to identify a foreign object other than the one or more vehicle systems that is contacting the conductive components of the route, or to identify a damaged or broken portion of at least one of the conductive components of the route.

In one aspect, at least one of the transmit monitor or the receive monitor is configured to examine the changes in the transmitted current and in the received current to both determine when at least one of the vehicles is disposed on the route and to identify the at least one of the contaminated portion, the foreign object, or the damaged or broken portion by identifying: (a) increases or decreases in the transmitted current and the received current and (b) time periods over which the increases or decreases in the transmitted current and the received current occur.

In one aspect, at least one of the transmit monitor or the receive monitor is configured to identify the contaminated portion of the surface as a portion of ballast material disposed beneath the conductive components of the route that at least partially conducts the transmitted current between the conductive components of the route through the contaminated portion of the surface.

In one aspect, at least one of the transmit monitor or the receive monitor is configured to identify the foreign object as one or more conductive bodies forming a short between the conductive components of the route.

In one aspect, at least one of the transmit monitor or the receive monitor is configured to identify the damaged or broken portion of the at least one of the conductive components of the route as a portion of the at least one of the conductive components that is separated through an entire cross-sectional area of the at least one of the conductive components.

In one aspect, at least one of the transmit monitor or the receive monitor is configured to identify the contaminated portion of the surface responsive to the changes in the transmitted current and in the received current including an increasing trend in the transmitted current over an extended period of time that concurrently occurs with a decreasing trend in the received current over the extended period of time.

In one aspect, at least one of the transmit monitor or the receive monitor is configured to identify the foreign object responsive to the changes in the received current including a decrease in the received current to zero current or approximately zero current and temporary changes in the received current being temporally correlated with temporary changes in the transmitted current.

In one aspect, at least one of the transmit monitor or the receive monitor is configured to identify the damaged or broken portion of the at least one of the conductive components of the route is identified responsive to the changes in the transmitted current and in the received current including a decrease in the transmitted current that occurs concurrently with an elimination of the received current.

In one aspect, the route includes a track over which rail vehicles travel and the conductive components include rails of the track.

In another embodiment, a wayside monitoring method includes measuring a transmitted current that is applied to a conductive rail of a track over which one or more rail vehicles travel at a first location and measuring a received current at a different, second location to the conductive rails of the track. The received current includes at least a portion of the transmitted current that is conducted through one or more of the conductive rails from the first location to the second location. The method also can include identifying changes in the transmitted current and in the received current over time in order to both identify when the one or more of the rail vehicles travel between the first location and the second location and when at least one of: ballast material disposed between the conductive rails becomes contaminated to at least partially form a short between the conductive rails, a foreign object other than the one or more rail vehicles forms the short between the conductive rails, or one or more of the conductive rails is damaged or broken between the first location and the second location.

In one aspect, the changes in the transmitted current and the changes in the received current indicate that the ballast material is contaminated when the transmitted current increases and the received current decreases over an extended period of time that is longer than a time period during which the one or more rail vehicles travel over the conductive rails between the first location and the second location at a track speed of the conductive rails.

In one aspect, the changes in the transmitted current and the changes in the received current indicate that the foreign object is forming the short between the conductive rails responsive to the transmitted current increasing and the received current concurrently decreasing, followed by one or more temporary changes in the transmitted current and one or more temporary changes in the received current occurring during common time periods.

In one aspect, the changes in the transmitted current and the changes in the received current indicate that one or more of the conductive rails is damaged or broken when the transmitted current decreases and the received current is concurrently eliminated.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

The invention claimed is:

1. A method comprising:
   with a monitoring system having a transmit monitor and a receive monitor electrically coupled to conductive components of a route that is traveled by plural vehicle systems, monitoring transmitted current that is injected into the conductive components at a first location;
   with the monitoring system, monitoring a received current that represents at least a portion of the transmitted current that is conducted through the conductive components of the route, the received current received at a second, spaced-apart location of the conductive components;
   at plural different points in time during which the plural vehicle systems travel over the route plural times, sampling the monitored received current with the monitoring system to generate plural sampled values of the monitored received current;
   with one or more processors, examining changes in the sampled values to identify a contaminated portion of a surface on which the conductive components of the route are disposed; and
   responsive to identifying the contaminated portion, one or more of:
      reporting one or more of the contaminated portion of the route to one or more of the vehicle systems,
      reporting the one or more of the contaminated portion of the route to a maintainer of the route to schedule cleaning or replacement of the contaminated portion of the route or to schedule installation of a resistive element to the route, or
      changing a status of a signal of the route.

2. The method of claim 1, wherein the changes that are examined include:
   increases or decreases in the sampled values; and
   time periods over which the increases or decreases in the sampled values occur.

3. The method of claim 1, wherein the method includes examining the changes in the sampled values to identify the contaminated portion of the surface on which the conductive components of the route are disposed, wherein the contaminated portion of the surface includes a portion of ballast material disposed beneath the conductive components of the route that at least partially conducts the transmitted current between the conductive components of the route through the contaminated portion of the surface.

4. The method of claim 1, wherein the method includes examining the changes in the sampled values to identify a foreign object other than the vehicle systems, and wherein the foreign object that is identified is one or more conductive bodies forming a short between the conductive components of the route and that are moveable relative to the conductive components of the route.

5. The method of claim 1, further comprising examining the changes in the sampled values to identify a damaged or broken portion of at least one of the conductive components of the route.

6. The method of claim 1, wherein the method includes examining the changes in the sampled values to identify the contaminated portion of the surface on which the conductive components of the route are disposed responsive to the changes including an increasing trend in the transmitted current that simultaneously occurs with a decreasing trend in the received current.

7. The method of claim 1, wherein the method includes examining the changes in the sampled values to identify a foreign object other than the vehicle systems responsive to the changes including a decrease in the received current to zero current or approximately zero current and temporary changes in the received current occurring simultaneously with temporary changes in the transmitted current.

8. The method of claim 1, further comprising examining the changes in the sampled values to identify a damaged or broken portion of at least one of the conductive components of the route responsive to the changes including a decrease in the transmitted current that occurs simultaneously with an elimination of the received current.

9. A monitoring system comprising:
   a transmit monitor including one or more processors configured to measure a transmitted current that is injected into conductive components of a route that is traveled by plural vehicle systems; and
   a receive monitor including one or more processors configured to measure a received current that represents at least a portion of the transmitted current that is conducted through the conductive components of the route, wherein the transmitted current and the received current are injected and received, respectively, at different spaced-apart points along the conductive components;
   wherein the receive monitor is configured to generate sampled values of the measured received current by sampling the measured received current at plural different points in time during which the plural vehicle systems travel over the route plural times;
   wherein at least one of the transmit monitor or the receive monitor is configured to examine changes in the sampled values to identify a contaminated portion of a surface on which the conductive components of the route are disposed; and
   wherein at least one of the transmit monitor or the receive monitor is configured to, responsive to one or more of identifying the contaminated portion, one or more of:

report the contaminated portion of the route to one or more of the vehicle systems, report the one or more of the contaminated portion of the route to a maintainer of the route to schedule cleaning or replacement of the contaminated portion of the route or to schedule installation of a resistive element to the route, or change a status of a signal of the route.

10. The system of claim 9, wherein the at least one of the transmit monitor or the receive monitor is configured to examine the changes by identifying:

increases or decreases in the sampled values; and time periods over which the increases or decreases in the sampled values occur.

11. The system of claim 9, wherein the at least one of the transmit monitor or the receive monitor is configured to identify the contaminated portion of the surface as a portion of ballast material disposed beneath the conductive components of the route that at least partially conducts the transmitted current between the conductive components of the route through the contaminated portion of the surface.

12. The system of claim 9, wherein the at least one of the transmit monitor or the receive monitor also is configured to identify a foreign object on the route based on the changes in the sampled values as one or more conductive bodies forming a short between the conductive components of the route and that are moveable relative to the conductive components of the route.

13. The system of claim 9, wherein the at least one of the transmit monitor or the receive monitor is configured to identify a damaged or broken portion of at least one of the conductive components of the route based on the changes in the sampled values.

14. The system of claim 9, wherein the at least one of the transmit monitor or the receive monitor is configured to identify the contaminated portion of the surface responsive to the changes in the sampled values including an increasing trend in the transmitted current simultaneously occurs with a decreasing trend in the received current.

15. The system of claim 9, wherein the at least one of the transmit monitor or the receive monitor is configured to identify a foreign object on the route responsive to the changes in the sampled values including a decrease in the received current to zero current or approximately zero current and temporary changes in the received current occurring simultaneously with temporary changes in the transmitted current.

16. The system of claim 9, wherein the at least one of the transmit monitor or the receive monitor is configured to identify a damaged or broken portion of at least one of the conductive components of the route responsive to the changes in the sampled values including a decrease in the transmitted current that simultaneously with an elimination of the received current.

17. A method comprising:

with a monitoring system having a transmit monitor and a receive monitor electrically coupled to conductive rails of a track over which rail vehicles travel, measuring a transmitted current that is applied to the conductive rails at a first location;

with the monitoring system, measuring a received current at a different, second location of the conductive rails of the track, the received current including at least a portion of the transmitted current that is conducted through the conductive rails from the first location to the second location;

with the monitoring system, generating plural sampled values of the measured transmitted current and of the measured received current at plural different points in time spanning a time period that encompasses the rail vehicles traveling over the rails plural times;

with one or more processors, identifying changes in the sampled values to identify ballast material disposed between the conductive rails becoming contaminated to at least partially form a short between the conductive rails; and responsive to identifying the contaminated ballast material, one or more of:

reporting one or more of the contaminated ballast material to one or more of the rail vehicles, reporting the one or more of the contaminated ballast material to a maintainer of the route to schedule cleaning or replacement of the contaminated ballast material or to schedule installation of a resistive element to the rails, or changing a status of a signal of the rails.

18. The method of claim 17, wherein the changes in the sampled values indicate that the ballast material is contaminated responsive to the transmitted current increasing and the received current simultaneously decreasing.

19. The method of claim 17, wherein the changes in the sampled values indicate that a foreign object is forming a short between the conductive rails responsive to the transmitted current increasing and the received current concurrently decreasing, followed by one or more temporary changes in the transmitted current and one or more temporary changes in the received current occurring simultaneously.

20. The method of claim 17, wherein the changes in the sampled values indicate that one or more of the conductive rails is damaged or broken responsive to the transmitted current decreasing and the received current being simultaneously eliminated.

* * * * *